United States Patent
Lai et al.

(10) Patent No.: US 6,635,684 B2
(45) Date of Patent: Oct. 21, 2003

(54) METHOD FOR PREPARING HYDROPHILIC POROUS POLYMERIC MATERIALS

(75) Inventors: Huey-Min Lai, Hsinchu (TW); Chun-Hui Chang, Taipei (TW); Chun-Jen Liao, Taipei (TW); Chin-Fu Chen, Taipei (TW); Kuei-Hung Wu, Miaoli (TW); Yuan-Chia Chang, Taipei (TW); Yu-Yen Jan, Hsinchu (TW); Tsung-Yi Mou, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 194 days.

(21) Appl. No.: 10/083,242

(22) Filed: Oct. 19, 2001

(65) Prior Publication Data

US 2002/0086977 A1 Jul. 4, 2002

(30) Foreign Application Priority Data

Dec. 20, 2000 (TW) ........................ 89127372 A

(51) Int. Cl.⁷ .................................................. C08J 9/00
(52) U.S. Cl. ....................................................... 521/50
(58) Field of Search ................................ 530/422, 427; 536/124, 127, 128; 521/61

(56) References Cited

U.S. PATENT DOCUMENTS

| | | | |
|---|---|---|---|
| 4,412,947 A | 11/1983 | Cioca | 260/123.7 |
| 4,522,753 A | 6/1985 | Yannas et al. | 260/123.7 |
| 5,489,304 A | 2/1996 | Orgill et al. | 623/623 |
| 5,723,508 A | 3/1998 | Healy et al. | 521/61 |
| 5,869,080 A | 2/1999 | McGregor et al. | 424/426 |

OTHER PUBLICATIONS

I.V. Yannas, et al.; Design of an Artificial Skin. I. Basic Design Priniciples; Journal of Biomedical Materials Research; vol. 14; 65–81; (1980).

N. Dagalakis, et al.; Design of an Artificial Skin. Part III. Control of Pore Structure; Journal of Biomedical Materials Research; vol. 14; 511–528; (1980).

C.J. Doillon, et al.; Collagen–Based Wound Dressings: Control of the Pore Structure and Morphology; Journal of Biomedical Materials Research; vol. 20; 1219–1228; (1986).

Primary Examiner—Morton Foelak
(74) Attorney, Agent, or Firm—Ladas & Parry

(57) ABSTRACT

The present invention discloses a method for preparing a hydrophilic porous polymeric material comprising the step of mixing a hydrophilic polymeric material with a hydrophobic material; solvent sintering the surface of the hydrophilic polymeric material with water or an aqueous solution; and removing the hydrophobic material contained within the hydrophilic polymeric material with a massive organic solvent. Thus, the hydrophilic porous polymeric material with high porosity and stable structure is rapidly mass produced.

22 Claims, 5 Drawing Sheets

METHOD FOR PREPARING HYDROPHILIC POROUS POLYMERIC MATERIALS

BACKGROUND OF THE INVENTION

1. Field of the Invention

The present invention relates to a method for preparing a hydrophilic porous polymeric material.

2. Description of the Prior Art

Recently, the micro-porous products formed by different processings of bio-absorbable polymeric materials (such as collagen and PLGA) are widely applied in medical treatment, such as drug delivery carriers, constructs for bone and cartilage regeneration, templates for three-dimensional cell cultures and bioreactor substrate material. Being obtained from the Extra Cellular Matrix (ECM) of animal soft tissue, the collagen is extremely compatible with organisms and thus has great potential in biomedical applications.

Conventional processes used to prepare the porous collagen are freeze drying processes and only a few are critical point drying processes or air drying processes. The above processes are based on the research of Yannas and Burke since 1980. Please refer to: Design of an artificial skin. I. Basic design principles, I. V. Yannas; John F. Burke, Journal of Biomedical Materials Research. Vol.14, 65–81 (1980); and Design of an artificial skin. Part III. Control of pore structure, N. Dagalakis, J. Flink, I. V. Yannas et al., Journal of Biomedical Materials Research Vol. 14, 511–528 (1980).

1. Freeze Drying Process

One of the most common processes in recent use to prepare porous materials is freeze drying process and its preparation theories are disclosed in U.S. Pat. Nos. 4,412,947, 4,522,753, 5,869,080 and 5,723,508. Natural polymeric materials are well dispersed in an aqueous solution or a solvent, and the mixture is frozen. After that, the water or solvent in the mixture is solidified as ice crystals. The ice crystal inside the frozen mixture is directly sublimed under a high vacuum condition so as to form a porous polymeric material.

The porous polymeric material formed by the freeze drying process, has a very wide range of pore size, which depends on the size of ice crystal. It is possible to obtain a porous polymeric material having a high porosity (about 90% by volume) with interconnecting pores. The pore size and pore structure are influenced by factors such as freezing temperature, the amount of water contained in the aqueous solution, pH value and uniformity of dispersion. In 1986, Doillon et al. illustrated that the lower the freezing temperature or the faster the rate of temperature decrease, the smaller the ice crystals. Thus, a porous polymeric material with a smaller pore size is also produced. That is, the size of the ice crystal is to a large degree controlled by different freezing temperatures or different rates of decreasing temperature. Please refer to: Collagen-based wound dressings: Control of the pore structure and morphology, C. J. Doillon et al., Journal of Biomedical Materials Research Vol. 20, 1219–1228 (1986). For example, the pore size of about 14 $\mu$m is prepared at a temperature of −80° C., the pore size of about 30 $\mu$m is prepared at −55° C., and the pore size of about 100 $\mu$m is prepared at −30° C.

The freeze drying process is the most common one to produce a porous polymeric material. The advantage of the freeze drying process is that the water or solvent contained in the frozen mixture will be sublimed from its frozen state so that the change of the pore structure influenced by the chemical and the physic change is slight. Moreover, different pore sizes of the material can be produced by controlling the size of the ice crystal. Other solvents need not be introduced during the preparation process.

The shape of ice crystal influences the pore shape of the porous material because the pore is created by sublimation of ice crystals. However, well controlling of ice crystal structure and uniformity of its size is not easy to be achieved. Moreover, the freeze drying is a phase separation process, the water or solvent inside the frozen mixture needs to be "sucked out" by a freezing dryer. Thus, the above process to form a porous polymeric material is quite expensive and time-consuming. In addition, the size of the porous polymeric material formed by the freeze drying process is difficult to be programmed. Besides, the porous polymeric material absorbs water easily and becomes wet. The porous polymeric material needs to be reacted with a cross-linking agent for a cross-linking reaction so as to keep the stability of the structure. However, the structure of the porous polymeric material is often tumbledown and damaged if the cross-linking reaction is performed in the solution. Thus, the cross-linking agent used for the cross-linking reaction is usually in its gaseous form, such as the gaseous glutaraldehyde, to prevent the pore structure from damage. The reaction of the gaseous glutaraldehyde has to be monitored for its connectration and residual amount. The residual glutaraldehyde can be removed by blowing with air or nitrogen, and it is very difficult to remove completely. The glutaraldehyde remaining in the porous polymeric material causes the tissue to calcify or toxify the cells. The above-mentioned factors are, therefore, unfavorable for a mass production of a porous polymeric material formed by the freeze drying process.

2. Critical Point Drying (CPD) Process

The critical point drying process is similar to the freeze drying process, except that the water or solvent (such as alcohol) used in the freeze drying process is replaced by a liquid carbon dioxide. The porous polymeric material is formed while the carbon dioxide is directly sublimed by heating. However, the porous polymeric material formed by this process will shrink about 70% and the diameter of the pore is about 15 micrometers. Therefore, the critical point drying process is usually applied to prepare samples of scanning electron microscope (SEM) in a laboratory, and is not applied for a mass production.

3. Air Drying Process

The air drying process is to evaporate the water or solvent contained in the polymeric material at room temperature. Different pore structures are formed while different solvents are used. The pore size formed by air drying process is not easy to control the size distribution and morphology. Moreover, the air drying process is also time-consuming and cannot produce a sponge-like product.

SUMMARY OF THE INVENTION

The first object of the present invention is to provide a method for preparing hydrophilic porous polymeric material, comprising the following steps:

(a) mixing a hydrophilic polymeric material with a hydrophobic material;

(b) solvent sintering the surface of the hydrophilic polymeric material by adding water or an aqueous solution; and (c) removing the hydrophobic material contained within the hydrophilic polymeric material with an organic solvent, which can dissolve the hydrophobic material, and solidifying the sintered hydrophilic polymeric material.

The second object of the present invention is to provide a method for rapidly mass producing the porous polymeric material. The pore size of the porous polymeric material and its porosity are controlled by the mixing ratio of the hydrophilic polymeric material and hydrophobic material and their particle sizes.

The third object of the present invention is to provide a method for preparing a hydrophilic porous polymeric material which further comprises a cross-linking step so as to improve its mechanical strength and the resistance to an acid and a base and to reduce the immunoreactions caused by implantation in humans.

The fourth object of the present invention is to provide a method for preparing a hydrophilic porous polymeric material, in which the pore and the composition can have a gradient distribution to meet various requirements for application.

DETAILED DESCRIPTION OF THE INVENTION

In order to achieve the above objects and to avoid the disadvantages of the prior art, the present invention discloses a method for rapidly mass producing a hydrophilic porous polymeric material with high porosity and stable structure, comprising the following steps:

(a) mixing a hydrophilic polymeric material with a hydrophobic material;

(b) solvent sintering the surface of the hydrophilic polymeric material by adding water or an aqueous solution; and (c) removing the hydrophobic material contained within the hydrophilic polymeric material with an organic solvent, which can dissolve the hydrophobic material, and solidifying the sintered hydrophilic polymeric material.

The hydrophilic polymeric material and the hydrophobic material of the present invention are mixed in their solid states.

The above mixture is dipped into water or an aqueous solution for solvent sintering whole of the surface of the hydrophilic polymeric material. Finally, an organic solvent is introduced into the mixture for solidifying the sintered hydrophilic polymeric material because its solubility is decreased. The hydrophobic material inside the mixture is thus washed out by the organic solvent. Therefore, the hydrophilic porous polymeric material with high porosity and interconnecting channel is rapidly mass produced. Since the massive organic solvent is introduced deeply into the polymeric material, the residual problem of the solvent is avoided. Furthermore, the hydrophilic porous polymeric material can be further modified by a cross-linking reaction and it is useful to facilitate a mass production by a continuous operation.

Figure 1A:
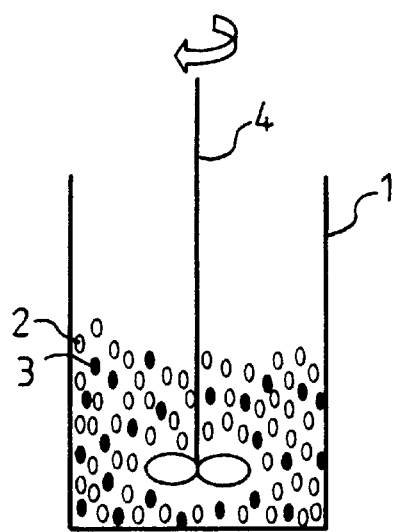
FIGS. 1a to 1d depict the steps of preparing a hydrophilic porous polymeric material according to one embodiment of the present invention.

Referring to FIG. 1(a), the hydrophilic polymeric material 3 and the hydrophobic material 2 are mixed well in their solid states in a vessel 1 by a stirring apparatus 4 for about 10 seconds to 5 minutes, preferably about 1 minute. The hydrophilic polymeric material 3 and the hydrophobic material 2 are mixed in an appropriate ratio, in which the weight percentage of the hydrophobic material 2 is about 50–95%, preferably 75–95%. The hydrophilic polymeric material 3 is granular or fibrous and may be a natural hydrophilic protein, a polysaccharide or their composites. The preferred hydrophilic polymeric material is selected from the group consisting of gelatin, collagen, chitin, chitosan, glucosaminoglycans, chondroitin sulfates, alginate, extracellular, starch, modified starch, carrageenin and its salts, pectin, fibrin, laminin, fibronectin, elastin and mixtures thereof. Moreover, the mixtures indicated in the hydrophilic polymeric material can be in the form of a composite, such as a composite of gelatin and collagen or a composite of gelatin and chitosan. The preferred hydrophilic polymeric material 3 is selected from the group consisting of gelatin, chitosan, a composite of gelatin and collagen (gelatin/collagen composite) and a composite of gelatin and chitosan (gelatin/chitosan composite). The hydrophobic material 2 is easy to dissolve in an organic solvent and may be selected from the group consisting of succinic anhydride, polyethylene glycol, polyethylene, polystyrene, polypropylene, polyvinyl chloride, polyvinyl fluoride, polyacrylic cellulose acetate, polyethylene terephthalate, polyamide and fatty acid.

Figure 1B:
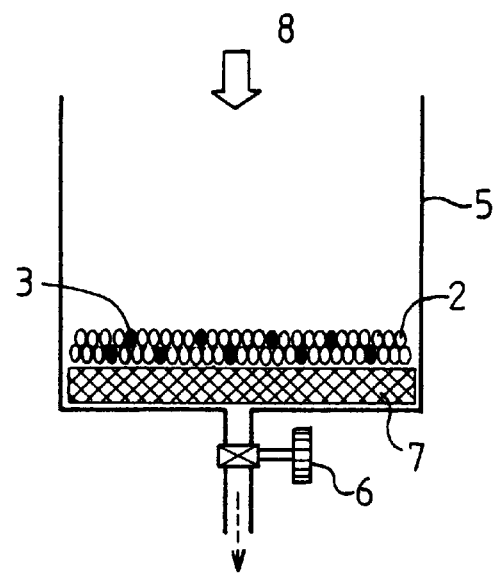

Referring to FIG. 1(b), the mixture of the hydrophilic polymeric material 3 and the hydrophobic material 2 is placed into a leach apparatus 5, which has a switch valve 6. The bottom of the leach apparatus 5 is covered with a nonstick net 7. Water or an aqueous solution 8 is poured into the leach apparatus 5. The aqueous solution 8 is a diluted acid solution or a diluted basic solution. The diluted acid solution is a diluted solution of an organic acid or an inorganic acid, wherein the pH value is between 2.5 and 5. The preferred organic acid is selected from the group consisting of acetic acid, citric acid, oxalic acid, lactic acid, tartaric acid, ascorbic acid and sorbic acid. The preferred inorganic acid is selected from the group consisting of hydrochloric acid, sulfuric acid, boric acid, phosphoric acid, sulphurous acid, nitrous acid and nitric acid. The pH value of the diluted basic solution is between 9 and 12. The preferred base used in the basic solution is selected from the group consisting of sodium hydroxide, sodium bicarbonate, potassium hydroxide, calcium hydroxide, ammonia, sodium citrate and sodium acetate. The mixture of the hydrophilic polymeric material 3 and the hydrophobic material 2 is dipped into water or the aqueous solution 8 for about 5 seconds to 5 minutes, preferable 10 seconds to 60 seconds, which is controlled by the switch valve 6. The surface of the hydrophilic polymeric material is then partially solvent sintered by water or the aqueous solution 8 so that the hydrophobic material is contained within the sintered hydrophilic polymeric material. Then water or the aqueous solution 8 is removed through the nonstick net 7 by gravitation filtration or being sucked away with a pressure difference provided by an air-suction.

Figure 1C:
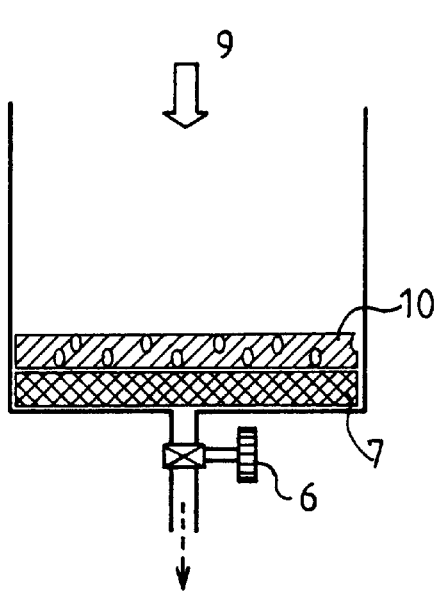

After water or the aqueous solution 8 is removed, please refer to FIG. 1(c), the massive organic solvent 9 is added into the leach apparatus 5. The sintered surface of the hydrophilic polymeric material 3 is solidified and the hydrophobic material 2 contained within the sintered hydrophilic polymeric material 3 is washed out by the organic solvent. The organic solvent 9 is selected from the group consisting of acetone, ethanol, n-hexane, benzene, toluene, decane, chloroform, ether, cyclohexanone, acetonitrile, tetrahydrofuran, benzoic acid, ethyl acetate, isopropanol and butanone. The organic solvent 9 is introduced to pass through the inside of the mixture of the hydrophilic polymeric material 3 and the hydrophobic material 2. Thus, the sintered hydrophilic polymeric material can be solidified since its solubility has been decreased and the hydrophobic material is also washed out. The mixture is dipped into the organic solvent 9 for from about 5 seconds to 5 minutes, which is also controlled by the switch valve 6. Then the organic solvent 9 is removed through the nonstick net 7. Therefore, the hydrophilic porous polymeric material with high porosity and interconnected channel is rapidly mass produced. In one preferred embodiment, the steps shown in FIGS. 1(b) and 1(c) are performed under a pressure difference condition for sintering the surface of the hydrophilic polymeric material and removing the hydrophobic material very quickly.

Figure 1D:
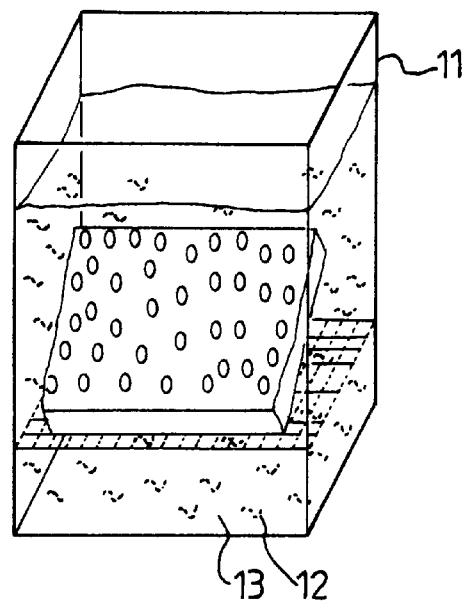

In another preferred embodiment, the process for producing a hydrophilic porous polymeric material of the invention further comprises a cross-linking step, shown in FIG. 1(d). The hydrophilic porous polymeric material is dipped into a cross-linking agent 12, which is preferably diluted with an organic solvent 13, to perform a cross-linking reaction. The cross-linking agent 12 is selected from the group consisting of epoxide, activated polyethylene glycol, glutaraldehyde, carbodiimide, isocyanate, borohydride, sulfur isocyanate and aldehyde. The organic solvent 13 is selected from the group consisting of acetone, ethanol, n-hexane, benzene, toluene, decane, chloroform, ether, cyclohexanone, acetonitrile, tetrahydrofuran, benzoic acid, ethyl acetate, isopropanol and butanone. The residual cross-linking agent will be washed out by the massive organic solvent after the cross-linking reaction, and the hydrophilic porous polymeric material with stable structure is thus obtained.

In order to meet the various requirements, the hydrophilic polymeric material comprises at least two different kinds of the hydrophilic polymeric materials, wherein the weight percentage of these hydrophilic polymeric materials are same or different. Furthermore, these hydrophilic polymeric materials with different particle sizes can be stacked for forming a gradient distribution structure of the hydrophilic porous polymeric material.

EXAMPLE 1

Method for Preparing the Collagen Porous Material

The hydrophilic polymeric material used in this example was collagen, which is extracted from animals, such as cattle. The collagen was pulverized by a pulverizer and sieved with a 60–80 meshes net so as to obtain collagen with a particle size of about 177–250 µm. The hydrophobic material in this example was succinic anhydride with a particle size of about 250 µm, and the organic solvent used to solve the succinic anhydride was acetone.

First, the collagen and the succinic anhydride were pulverized into particles with the above-mentioned particle size, respectively. The collagen and the succinic anhydride were mixed well and the succinic anhydride was 85% by weight. The diluted acidic solution was poured into the mixture to solvent sinter the surface of the collagen particles, meanwhile the succinic anhydride particles were contained within the sintered collagen particle. After 20 seconds, acetone was introduced massively to wash the succinic anhydride out, which was contained within the sintered collagen particles, and a porous polymeric material with interconnected channel was formed. The sintered collagen particles were also solidified because of the acetone. Finally, the collagen, which has been solidified, was placed into a beaker with acetone to wash out the residual succinic anhydride. A 0.5% (w/v) glutaraldehyde solution diluted with acetone was added to perform the cross-linking reaction.

Figure 2A:
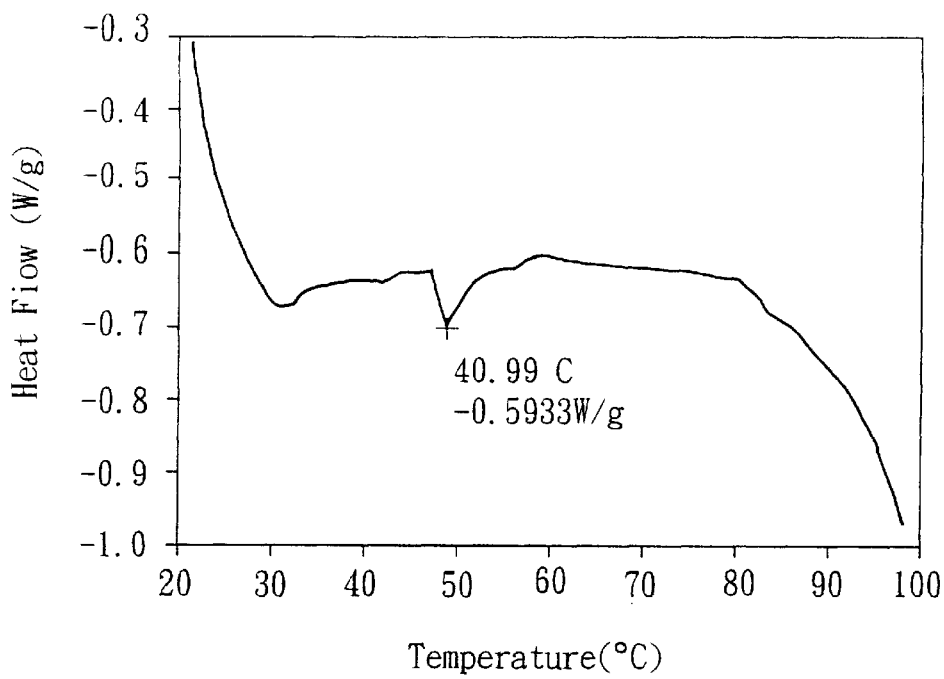
FIG. 2a depicts a differential scanning calorimeter (DSC) analysis chart of one embodiment before the cross-linking reaction is carried out according to the present invention.
Figure 2B:
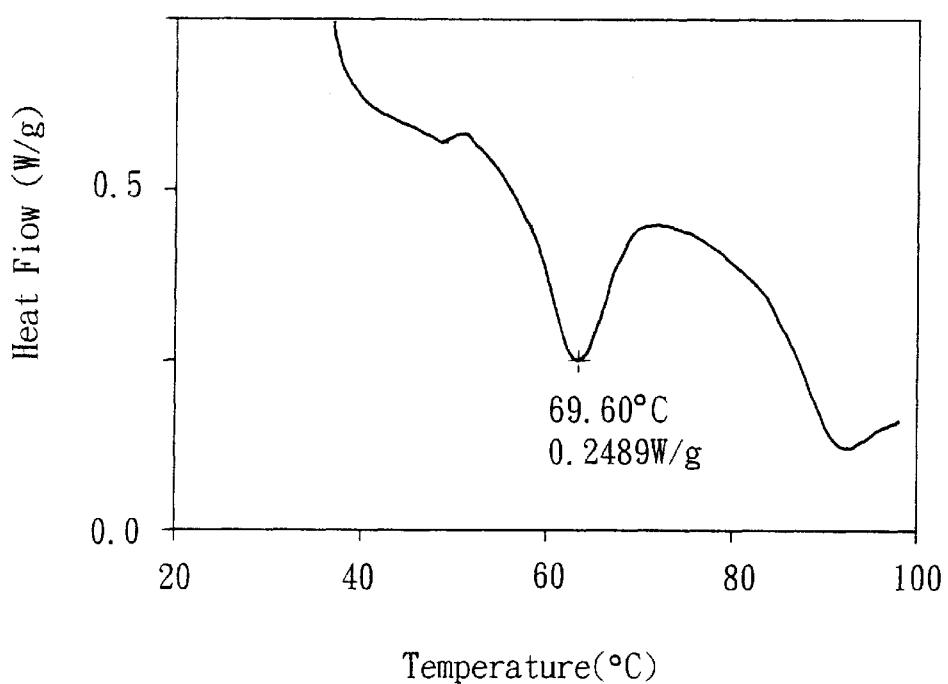
FIG. 2b depicts a differential scanning calorimeter (DSC) analysis chart of one embodiment after the cross-linking reaction is carried out according to the present invention.
Figure 3:
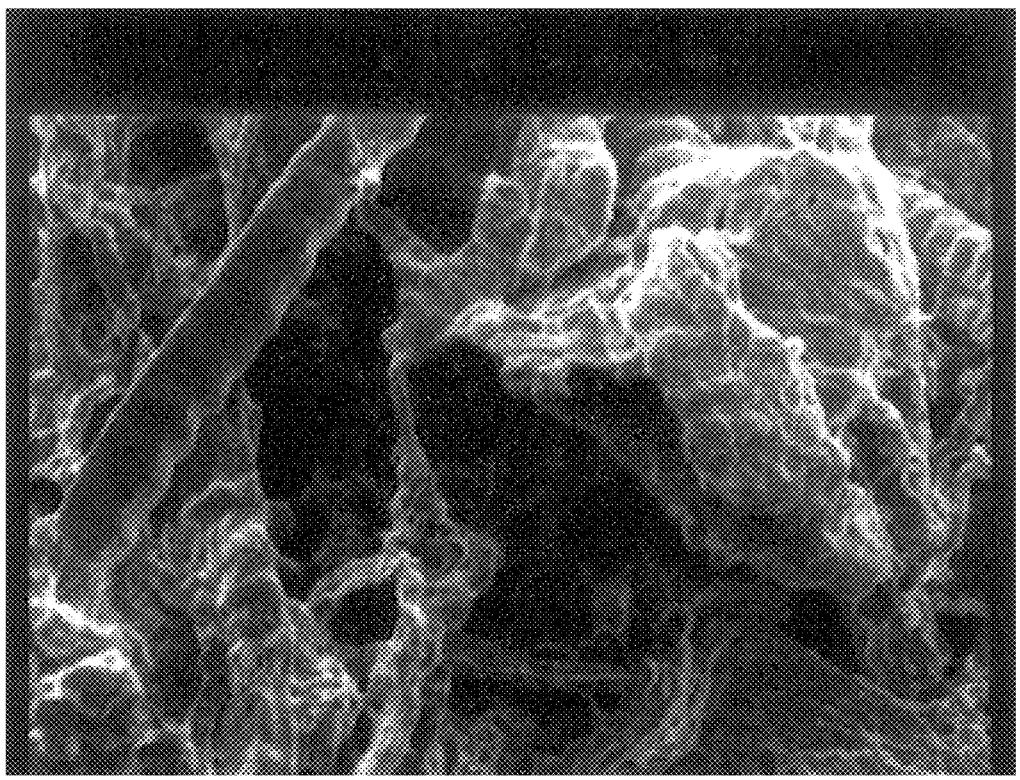
FIG. 3 depicts a scanning electron microscope (SEM) result of the hydrophilic porous polymeric material of Example 1 of the present invention.

After the cross-linking reaction, the denature temperature of the hydrophilic porous polymeric material was increased from 49° C. to 63.60° C., measured by the differential scanning calorimeter (DSC), shown in FIG. 2. The pore size of the hydrophilic porous polymeric material of the present invention was 200 µm measured by the scanning electron microscope (SEM), shown in FIG. 3.

EXAMPLE 2

Method for Preparing the Gelatin Porous Material

The hydrophilic polymeric material used in this example was gelatin with gel strength of 80–100 g/cm$^2$, which is extracted from animals, such as cattle. The gelatin was pulverized by a pulverizer and sieved with a 60–80 meshes net. The particle size of the gelatin is about 177–250 µm. The hydrophobic material of this example was succinic anhydride with a particle size of about 250 µm, and the organic solvent used to solve the succinic anhydride was acetone.

First, the gelatin and the succinic anhydride were pulverized into particles with the above-mentioned particle size, respectively. The gelatin and the succinic anhydride were mixed well and the succinic anhydride was 85% by weight. The diluted acidic solution was poured into the mixture to solvent sinter the surface of the gelatin particles, meanwhile the succinic anhydride particles were contained within the sintered gelatin particles. After 20 seconds, acetone was added massively to wash the succinic anhydride out, which was contained within the sintered gelatin, and a hydrophilic porous polymeric material with interconnected channel was formed. The sintered gelatin particles were also solidified because of the acetone. Finally, the gelatin, which has been solidified, was placed into a beaker with acetone to wash out the residual succinic anhydride. Then, a 0.5% (w/v) glutaraldehyde solution diluted with acetone was added to perform the cross-linking reaction.

Figure 4:
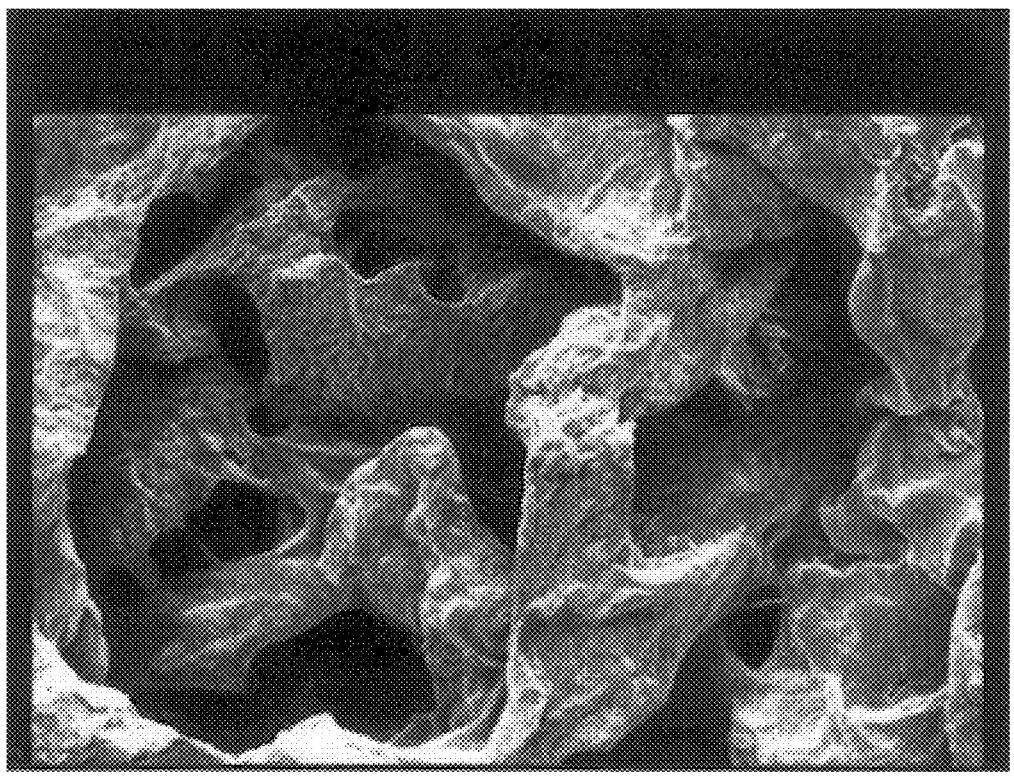
FIG. 4 depicts a scanning electron microscope (SEM) result of the hydrophilic porous polymeric material of Example 2 of the present invention.

The pore size of the obtained hydrophilic porous polymeric to material was 500 µm, measured by the scanning electron microscope (SEM), shown in FIG. 4.

EXAMPLE 3

Method for Preparing the Chitosan Porous Material

The hydrophilic polymeric material used in this example was chitosan, which was obtained by being extracted from shellfish, such as shrimp or crab, and then proceeded with a deacetylation step. The deacetylation degree of the chitosan is about 90%. The chitosan was pulverized by a pulverizer and then sieved with a 60–80 meshes net. The particle size of the chitosan is about 177–250 µm. The hydrophobic material of this example was succinic anhydride with a particle size of about 250 µm, and the organic solvent used to solve the succinic anhydride was acetone.

First, the chitosan and the succinic anhydride were pulverized into particles with the above-mentioned particle size, respectively. The chitosan and the succinic anhydride were mixed well and the succinic anhydride was 85% by weight. The diluted acidic solution was poured into the mixture to solvent sinter the surface of the chitosan particles, meanwhile the succinic anhydride particles were contained within the sintered collagen particles. After 20 seconds, acetone was introduced massively to wash the succinic anhydride out, which was contained within the sintered chitosan particles, and a porous polymeric material with interconnected channel was formed. The sintered chitosan particles were also solidified because of the acetone. Finally, the chitosan, which had been solidified, was placed into a beaker with acetone to wash out the residual succinic anhydride. Then, a 0.5% (w/v) glutaraldehyde solution diluted with acetone was added to perform the cross-linking reaction.

Figure 5:
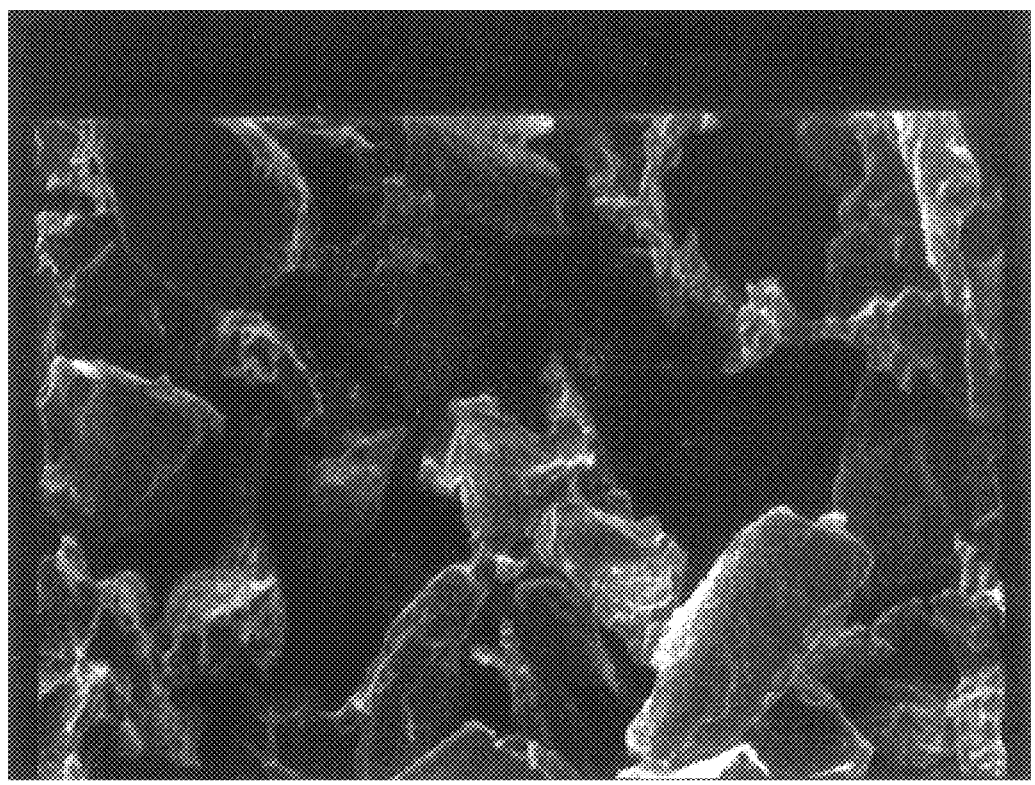
FIG. 5 depicts a scanning electron microscope (SEM) result of the hydrophilic porous polymeric material of Example 3 of the present invention.

The pore size of the obtained hydrophilic porous polymeric material was 300 μm, measured by the scanning electron microscope (SEM), shown in FIG. 5.

EXAMPLE 4

Method for Preparing the Mixed Chitosan/Gelatin Porous Material

The hydrophilic polymeric materials used in this example were gelatin with gel strength of 80–100 g/cm$^2$ and chitosan with a deacetylation degree of above 70%. The gelatin is obtained from animals, such as cattle. The chitosan was obtained from shellfish, such as shrimp or crab, which was proceeded with a deacetylation step. Both chitosan and gelatin were pulverized by a pulverizer and sieved with a 60–80 meshes net. The particles size of chitosan and gelatin were about 177–250 μm. The hydrophobic material of this example was succinic anhydride with a particle size of about 250 μm, and the organic solvent used to solve the succinic anhydride was acetone.

First, the chitosan and the gelatin were mixed in a weight ratio of 1:1. The mixture of chitosan, gelatin and succinic anhydride was pulverized into particles with the above-mentioned particle size, respectively. The chitosan, the gelatin and the succinic anhydride were mixed well, in which the succinic anhydride was 85% by weight. The diluted acidic solution was poured into the mixture to solvent sinter the surface of the chitosan and the gelatin particles, meanwhile the succinic anhydride particles were contained within the sintered chitosan particles and the gelatin particles. After 20 seconds, acetone was introduced massively to wash the succinic anhydride out, which was contained within the sintered chitosan and gelatin, and a hydrophilic porous polymeric material with interconnected channel was formed. The sintered chitosan particles and gelatin particles were also solidified because of the acetone. Finally, the chitosan and the gelatin, which had been solidified, were placed into a beaker with acetone to wash out the residual succinic anhydride. Then, a 0.5% (w/v) glutaraldehyde solution diluted with acetone was added to perform the cross-linking reaction.

The pore size of the obtained hydrophilic porous polymeric material was measured with the scanning electron microscope (SEM).

The methods and features of this invention have been sufficiently described in the above examples and descriptions. It should be understood that any modifications or changes without departing from the spirit of the invention are intended to be covered in the protection scopes of the invention.

What is claimed is:

1. A method for preparing a hydrophilic porous polymeric material comprising the following steps:
   (a) mixing a hydrophilic polymeric material with a hydrophobic material;
   (b) solvent sintering the surface of the hydrophilic polymeric material by adding water or an aqueous solution; and
   (c) removing the hydrophobic material with an organic solvent, which can dissolve the hydrophobic material, and solidifying the sintered hydrophilic polymeric material.

2. The method of claim 1, further comprising a cross-linking step after step (c).

3. The method of claim 1, wherein the hydrophilic polymeric material and the hydrophobic material of step (a) are mixed in their solid states.

4. The method of claim 1, which comprises at least one hydrophilic polymeric material is used in step (a).

5. The method of claim 1, wherein the hydrophilic polymeric material of step (a) comprises two or more particle sizes.

6. The method of claim 1, wherein the hydrophilic polymeric material of step (a) is selected from the group consisting of gelatin, collagen, chitin, chitosan, glucosaminoglycans, chondroitin sulfates, alginate, extracellular, starch, modified starch, carrageenin and its salts, pectin, fibrin, laminin, fibronectin, elastin and mixtures thereof.

7. The method of claim 6, wherein the hydrophilic polymeric material is selected from the group consisting of gelatin, chitosan, a gelatin/collagen composite and a gelatin/chitosan composite.

8. The method of claim 1, wherein the hydrophilic polymeric material of step (a) is granular or fibrous.

9. The method of claim 1, wherein the hydrophobic material of step (a) is selected from the group consisting of succinic anhydride, polyethylene glycol, polyethylene, polystyrene, polypropylene, polyvinyl chloride, polyvinyl fluoride, polyacrylic cellulose acetate, polyethylene terephthalate, polyamide and fatty acid.

10. The method of claim 1, wherein the aqueous solution of step (b) is a diluted acidic solution or a diluted basic solution.

11. The method of claim 10, wherein the pH value of the diluted acidic solution is between 2.5 and 5.

12. The method of claim 10, wherein the pH value of the diluted basic solution is between 9 and 12.

13. The method of claim 10, wherein the acidic solution is an organic acid solution or an inorganic acid solution.

14. The method of claim 13, wherein the organic acid is selected from the group consisting of acetic acid, citric acid, oxalic acid, lactic acid, tartaric acid, ascorbic acid and sorbic acid.

15. The method of claim 13, wherein the inorganic acid is selected from the group consisting of hydrochloric acid, sulfuric acid, boric acid, phosphoric acid, sulphurous acid, nitrous acid and nitric acid.

16. The method of claim 10, wherein the base used the diluted basic solution is selected from the group consisting of the sodium hydroxide, sodium bicarbonate, potassium hydroxide, calcium hydroxide, ammonia, sodium citrate and sodium acetate.

17. The method of claim 1, wherein steps (b) and (c) are performed under a pressure difference condition.

18. The method of claim 1, wherein the organic solvent of step (c) is selected from the group consisting of acetone, ethanol, n-hexane, benzene, toluene, decane, chloroform, ether, cyclohexanone, acetonitrile, tetrahydrofuran, benzoic acid, ethyl acetate, isopropanol and butanone.

19. The method of claim 2, wherein the cross-linking reaction of the hydrophilic polymeric material is performed by reacting with a cross-linking agent.

20. The method of claim 19, wherein the cross-linking agent is diluted with an organic solvent.

21. The method of claim 20, wherein the organic solvent is selected from the group consisting of the acetone, ethanol, n-hexane, benzene, toluene, decane, chloroform, ether, cyclohexanone, acetonitrile, tetrahydrofuran, benzoic acid, ethyl acetate, isopropanol and butanone.

22. The method of claim 19, wherein the cross-linking agent is selected from the group consisting of the epoxide, activated polyethylene glycol, glutaraldehyde, carbodiimide, isocyanate, borohydride, sulfur isocyanate and aldehyde.

* * * * *